United States Patent

Crombie et al.

[11] Patent Number: 5,226,906
[45] Date of Patent: Jul. 13, 1993

[54] SURGICAL SPEED WRENCH

[75] Inventors: John S. Crombie, Irvington, N.J.; Martin H. Krag, Colchester, Vt.

[73] Assignee: Howmedica, Inc., New York, N.Y.

[21] Appl. No.: 654,711

[22] Filed: Feb. 13, 1991

[51] Int. Cl.[5] .............................................. A61F 5/04
[52] U.S. Cl. ..................................... 606/61; 606/104; 606/86; 81/57.3
[58] Field of Search ................. 81/57.3, 57.29, 13, 81/55; 606/60, 61, 86, 96, 99, 104

[56] References Cited

U.S. PATENT DOCUMENTS

| | | | |
|---|---|---|---|
| 1,265,144 | 5/1918 | Van Sickle | 81/57.3 |
| 1,487,785 | 3/1924 | Knowles | 81/57.3 |
| 2,482,387 | 8/1947 | Veneman | 81/57.3 |
| 2,601,798 | 7/1952 | Spence | 81/57 |
| 3,027,789 | 4/1962 | Bochman | 81/57.3 |
| 3,603,132 | 9/1971 | Holmes | 81/55 |
| 3,618,430 | 11/1971 | Wieck | 81/57.3 |
| 3,987,691 | 10/1976 | Savage | 81/57.3 |
| 4,140,161 | 2/1979 | Russo | 145/52 |
| 4,374,480 | 2/1983 | Diaz | 81/57.3 |
| 4,406,188 | 9/1983 | Mills | 81/13 |
| 4,620,459 | 11/1986 | Singleton | 81/57.29 |
| 4,680,994 | 7/1987 | Singleton | 81/57.29 |
| 4,987,892 | 1/1991 | Krag | 606/61 |

Primary Examiner—Robert A. Hafer
Assistant Examiner—David J. Kenealy
Attorney, Agent, or Firm—Pennie & Edmonds

[57] ABSTRACT

A surgical speed wrench useful in installing spinal implant devices is provided with a thin profile and means for holding a part to be installed with a threaded fastener. The thin profile is achieved by a socket formed directly in a torque transmitting gear. The threaded fastener head is received directly in the socket and no other tool or adapter is required which would increase the profile. The holding means includes two extending arms terminating in spherical members which biasly engage a bore in the part to be installed. With the part thus held, the threaded fastener is received in the wrench socket and may be started and driven without the surgeon using his or her fingers or other instruments.

23 Claims, 5 Drawing Sheets

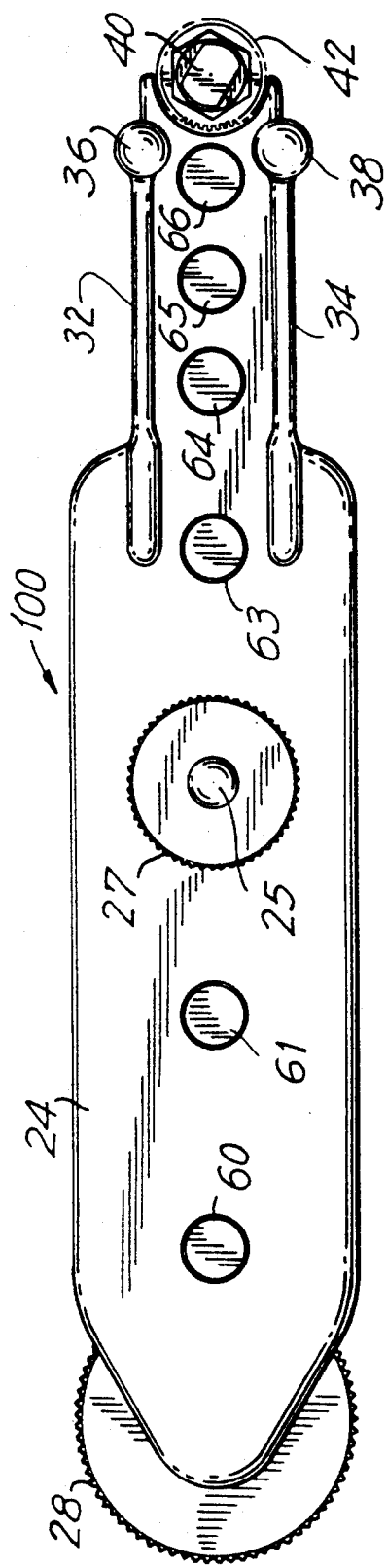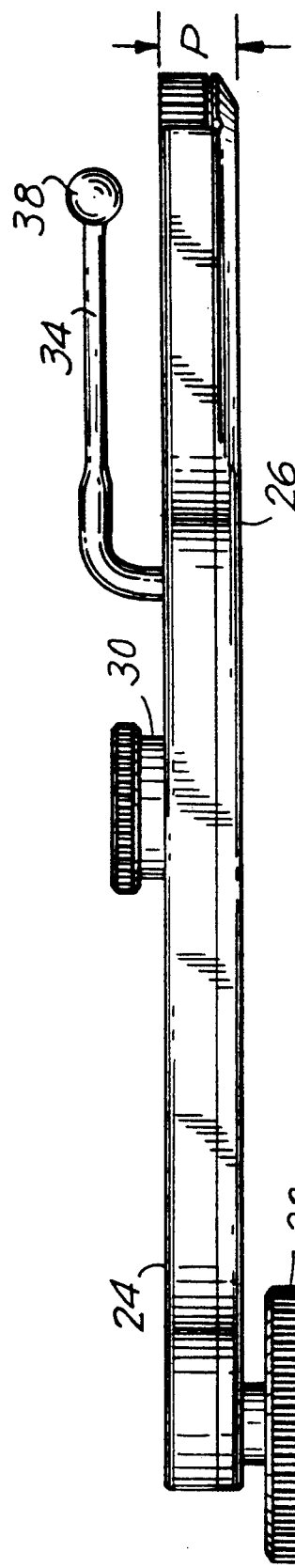

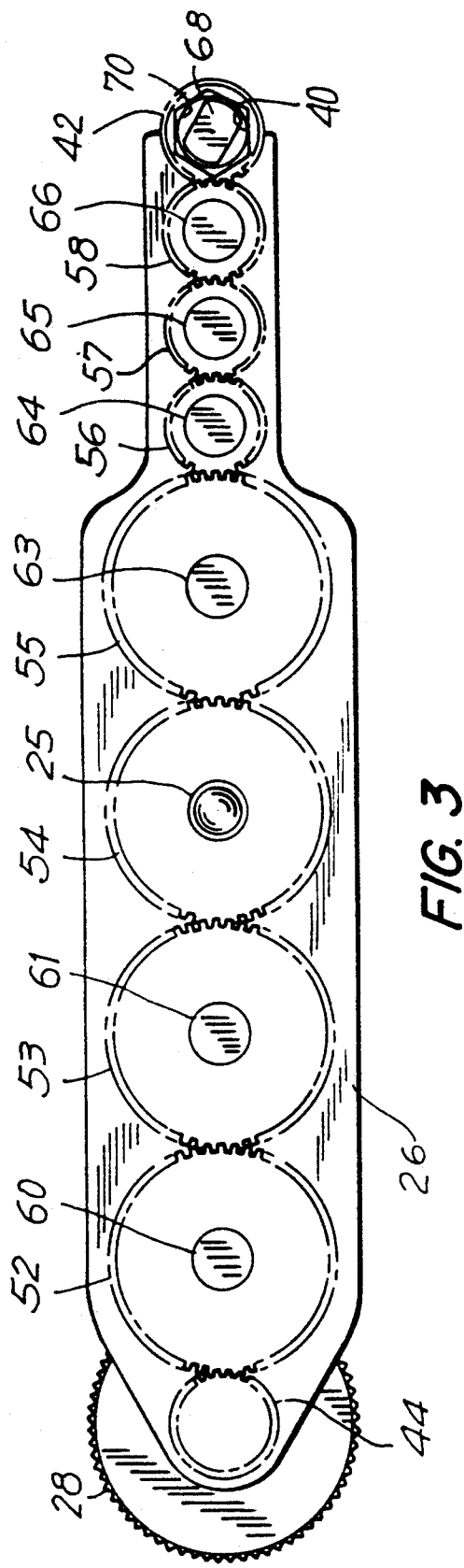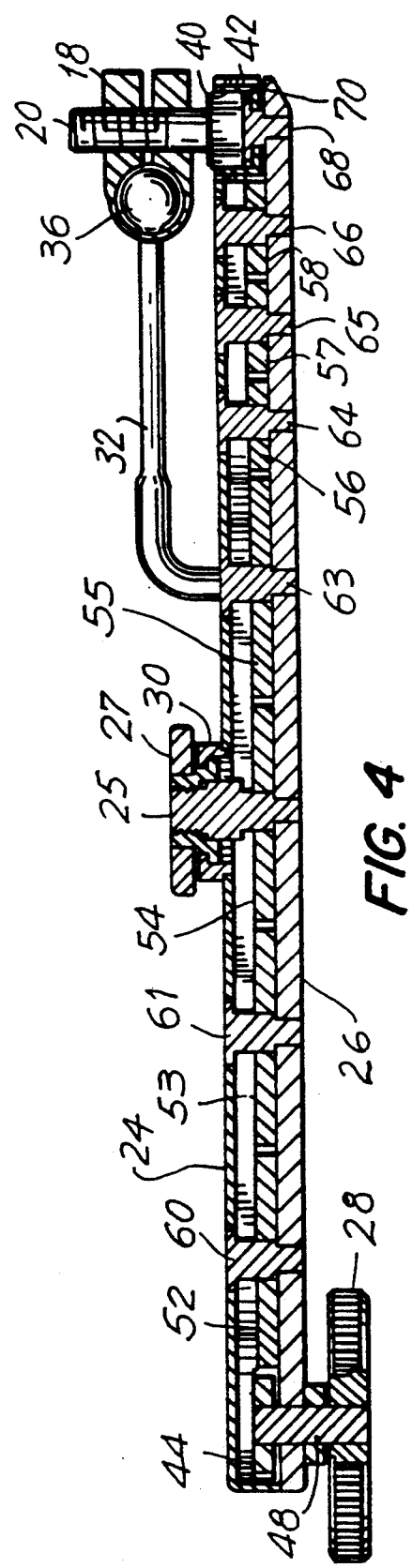

SURGICAL SPEED WRENCH

BACKGROUND OF THE INVENTION

The present invention relates to surgical instruments, and more particularly to a surgical wrench for simultaneously driving a bolt and holding in place a part through which the bolt is driven, until the bolt has been tightened.

Although not part of the present invention, a basic understanding of surgical implants that may be installed using the present invention is important to the understanding of the invention. The Vermont Spinal Fixator (VSF) is one such device. FIG. 7 illustrates a Vermont Spinal Fixator device 10 in place on a spinal column. FIG. 8 is an exploded view showing the relationship of the various components of the VSF. The fixator device is designed to rigidly fix together two spinal vertebrae surrounding a fractured vertebrae and, thus, fuse the spine around the fractured vertebrae. The Vermont Spinal Fixator is disclosed in detail in Krag et al., *An Internal Fixator for Posterior Application to Short Segments of the Thoracic, Lumbar, or Lumbosacral Spine*, Clinical Orthopaedics and Related Research, 203: 75-98, (Feb. 1986), incorporated by reference herein.

In order to implant the fixator device 10, holes are drilled in the appropriate vertebrae through surface A overlying the pedicle on either side of each vertebrae. After the holes are drilled, pedicle screws 12 are screwed into the pedicle using a shaft handle which is attached to flats 16 provided on the top of each screw 12. Once the pedicle screws 12 are in place in each of the four pedicles, an articulating clamp 18 is attached to each pedicle screw 12 with a clamp bolt 20.

After the articulating clamps 18 are in place, the clamp bolts 20 are initially left somewhat loose to allow for the assembly of connecting rods 22 between the two pedicle screws 12 on both sides of the fractured vertebra. After the fractured spine has been appropriately aligned, the clamp bolts 20 are tightened to permanently fix the spine and isolate the fractured vertebra.

In the past, surgeons have had difficulty in starting the clamp bolts 20 in threaded holes 14 provided in each pedicle screw 12. Part of the reason for the difficulty is that the clamp bolt 20 passes through articulating clamp 18, which must be held in place while the bolt is started. In addition, the space between the spinous process B and the installed pedicle screw is limited and the incision made for this procedure is relatively small. There is generally not room for the surgeon to reach into the incision and start the bolt 20 with his fingers while holding the articulating clamp 18 in place. Additionally, the components are small and relatively slippery during the operation, rendering their manipulation by hand difficult even if sufficient room was available. The limited space between spinous process B and pedicle screw 12 makes the use of known wrenches problematic.

In the past, surgeons have attempted to hold the articulating clamp in place with forceps while spinning the head of the bold with another instrument. Although workable, this method is slow, cumbersome and technically very difficult.

Low profile wrenches for use in surgical procedures are known, such as the "Twin Cities Spinal Wrench" by the Twin City Surgical Company designed for use in installing threaded nuts on threaded Harrington compression rods. This wrench utilizes a flat meshing gear train for transmitting torque to an end gear having a open-end wrench configuration for receiving nuts to be torqued.

U.S. Pat. No. 4,374,480 to Diaz discloses an extension tool for torquing screw fasteners located in restricted access areas. The Diaz extension tool is provided with a flat meshing gear train wherein the gears are supported by being disposed in close fitting circular recesses instead of on shafts, in order to reduce the thickness of the tool. The first and last gears are provided with multifaceted recesses for receiving commercially available torquing tools.

These wrenches are illustrative of the prior art, which, in general, does not provide a device suitable for the task of installing parts fixed by threaded fasteners such as articulating clamps and clamp bolts in surgical implants such as the VSF.

SUMMARY OF THE INVENTION

Therefore, an object of the present invention is to provide a surgical wrench having a profile which allows access to the limited space available in the installation of spinal fixation implants. A feature of present invention which assists in achieving this object is a drive means that includes a socket formed directly in a driven gear. This design decreases the overall profile of the wrench by eliminating the need for a socket tool or other adapter because the bolt to be driven is received directly in the gear which applies the torque.

A further object of the invention is to provide means for holding a part in place while a threaded fastener is driven therethrough. In this regard, the present invention provides a holding means comprising two adjacent arms that biasly engage the part to be held in a position that allows the threaded fastener to be engaged at the same time by the wrench. This feature prevents the need for separately holding the part to be installed while the threaded fastener is started.

Thus, according to the present invention an apparatus for installing a first part on a second part utilizing a threaded fastener passing through the first part and engaging the second part generally comprises a body, a driven gear mounted in the body with the driven gear having a drive means for directly engaging the threaded fastener without an adapter or other intermediate tool. In a preferred embodiment, the drive means includes a socket formed directly in the driven gear and configured to receive a hex-head threaded fastener. A drive gear and at least one intermediate gear are provided to transfer externally applied torque to the driven gear.

A means for holding the first part adjacent to the body with the threaded fastener passing through the first part and engaging the drive means is provided. In a preferred embodiment the holding means includes two adjacent arms, extending from one side of the body in the direction of the drive means, with the arms adapted to biasly engage the first part therebetween. To assist in engaging the first part, the arms may be provided with spherical members cooperating with an the connecting rod bore in the first part.

BRIEF DESCRIPTION OF THE DRAWING

The invention will be better understood if reference is made to the accompanying drawing, in which:

FIG. 1 is a top plan view of one embodiment of the wrench according to the present invention;

FIG. 2 is a side elevation of the wrench shown in FIG. 1;

FIG. 3 is a top plan view of the wrench shown in FIG. 1 with the cover plate removed to reveal the gear train;

FIG. 4 is a cross-sectional view of the wrench shown in FIG. 1, with an articulating clamp and clamp bolt installed thereon;

DETAILED DESCRIPTION OF THE PREFERRED EMBODIMENTS

Figure 5:
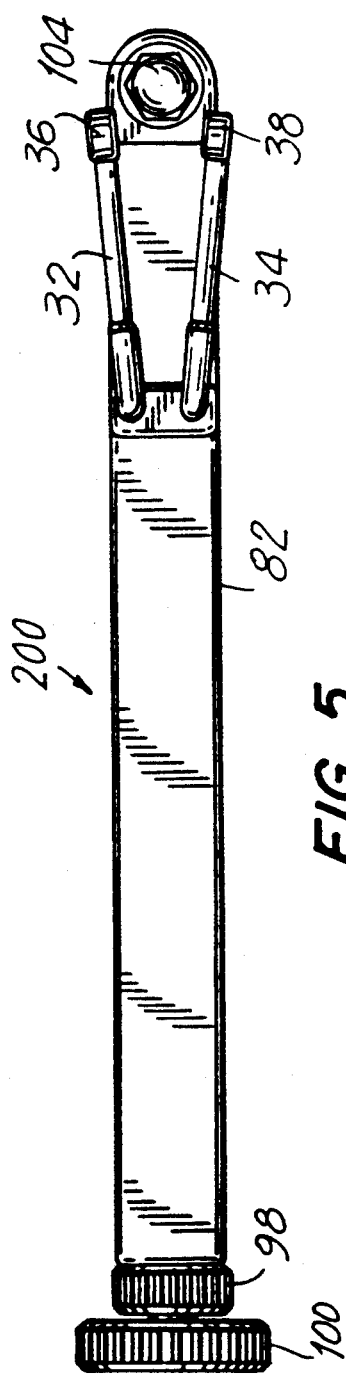
FIG. 5 is a top plan view of an alternative embodiment of the wrench according to the present invention.

Referring to FIGS. 1 and 2, wrench 100 according to one embodiment of the present invention is provided with a cover plate 24 and base plate 26 which supports the various other components of the wrench. Wheel 27 is screwed on to shaft 25 in order to fasten together cover plate 24 and base plate 26. As can be seen in FIG. 4, shaft 25 fits into base plate 26 and wheel 27 is rotatably retained by collar 30, which fits into cover plate 24. Shaft 25 and collar 30 can be permanently secured in base plate 26 and cover plate 24, respectively, by welding.

Extending from cover plate 24 are two arms 32 and 34 which terminate in engaging members 36 and 38, respectively. Engaging members 36 and 38, shown as balls in FIGS. 1, 2 and 4 cooperate with the connecting rod receiving bore 19 of the articulating clamp 18 to firmly grasp the articulating clamp due to a biasing force applied by arms 32 and 34. As illustrated in FIG. 4, when grasped between arms 32 and 34, articulating clamp 18 is disposed with hole 14, which receives clamp bolt 20, aligned with socket 40. Socket 40 receives and engages the head of bolt 20 for the application of torque by the wrench.

The drive train of wrench 100 comprises a number of spur gears that transmit torque from wheel 28 to socket gear 42. As shown in FIGS. 3 and 4, wheel 28 is fixed to drive gear 44 by shaft 48. Drive gear 44 cooperates with gear 52; thus, from drive gear 44 torque is transmitted forward by the cooperating engagement of gears 52–58. Gear 58 engages and drives socket gear 42. Gears 52, 53 and 55–58 are all similarly mounted on shaft pins 60, 61 and 63–66, which fit into base plate 26 and can be permanently secured by welding. As can be seen in FIG. 4, the thickness of the spur gears is only slightly greater than half of the height of the space provided between base plate 26 and cover plate 30. This allows the spur gears to slide on the shaft pins to provide a clearance for cleaning behind the gears. The thickness of the gears ensures that each gear always contacts at least a portion of the neighboring gears.

To provide a shape more conducive to manipulation in the surgical area, gears 56–58 are approximately one half of the diameter of gears 52–55. In a preferred embodiment gears 52–55 have a pitch radius of about ⅛ inch. It is also preferred that the gear ratio between wheel 28 and socket gear 42 is 1:1. Of course, the ratio could be varied to increase the torque applied by socket gear 42 or to increase the speed of operation, without departing from the teachings of the invention.

Due to the limited space between the pedicle screw 12 and spinous process B, there is not sufficient room for a standard type socket tool to grip the head of clamping bolt 20 in order to start the bolt in the pedicle screw 12. Therefore, the present invention provides socket gear 42 with socket 40 formed directly therein. Socket gear 42 is mounted on shaft pin 68, which is shaped with a head that is received in a further circular recess 70 within socket 40, in order to avoid interference with the head of bolt 20 when received in socket 68. In this manner, the overall profile of the wrench is significantly reduced to allow the wrench, with articulating clamp 18 and clamp bolt 20 attached, to fit into a limited space, such as that between the spinous process B and installed pedicle screw 12. With wrench 100, a profile (P as shown in FIG. 2) of approximately ⅜ inch or less is possible.

It is possible to further reduce the profile of wrench 100 by utilizing an alternative drive means such as a plastic pulley and belt system. With such a drive means the outside configuration of the wrench would remain substantially unchanged. A socket pulley, configured substantially as is socket gear 42, described above, would be utilized in connection with a drive pulley rotated by wheel 28.

Figure 6:
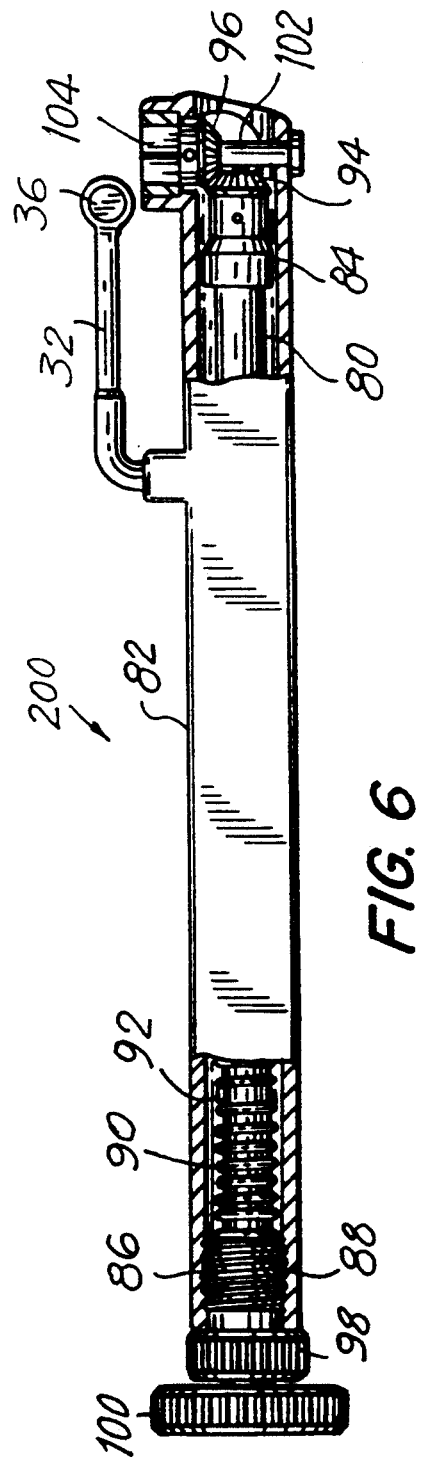
FIG. 6 is a partial cross-sectional side elevation view of the wrench of FIG. 5.

FIGS. 5 and 6 illustrate wrench 200 according to an alternative embodiment of the present invention. Shaft 80 is supported within casing 82 by bearing 84 at one end and cylindrical bushing 86 at the other. Bearing 84 is fixed to shaft 80 and rides on casing 82. Cylindrical bushing 86 has external screw threads 88 which mate with internal threads in casing 82. Bushing 86 is thus fixed to casing 82 and shaft 80 rides within a cylindrical bore through the bushing. Spring 90 acts between pin 92 and bushing 86 to bias shaft 80 and bevel gear 94, mounted the shaft, against cooperating bevel gear 96. Bushing 86 is provided with thumb wheel 98 to facilitate tightening of the screw threads. Thumb wheel 100 is provided for rotating shaft 80.

Figure 7:
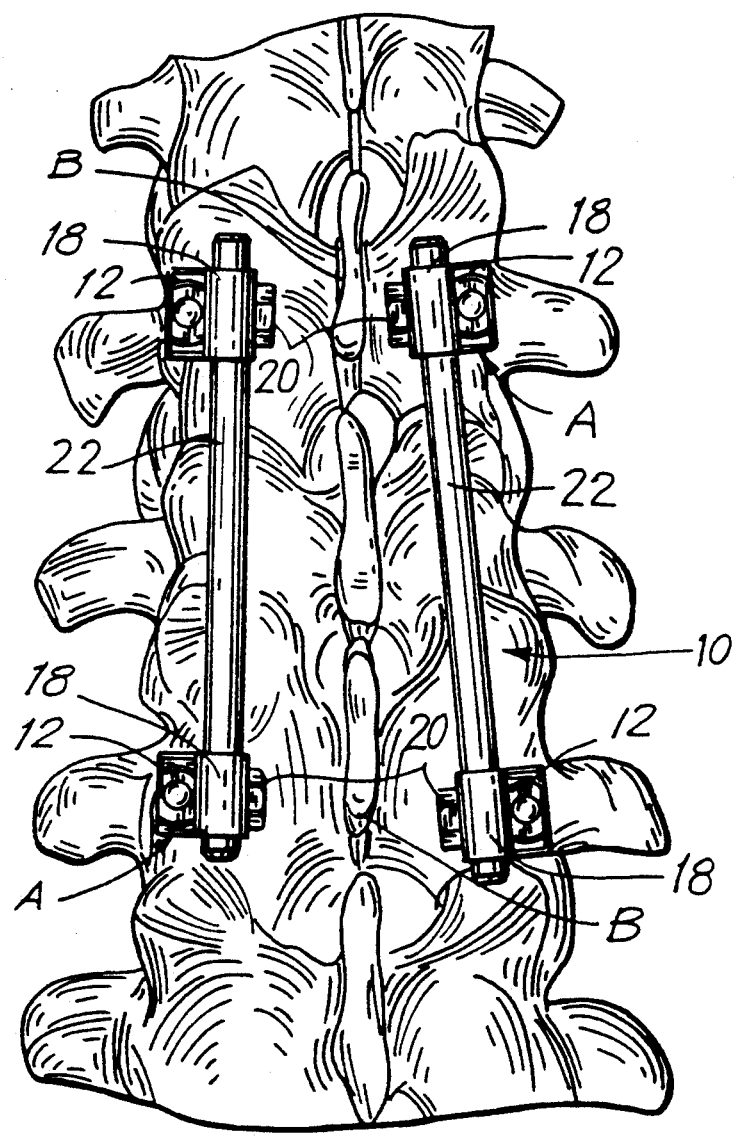
FIG. 7 is a dorsal plan view of a Vermont Spinal Fixator implant in place on a spine.
Figure 8:
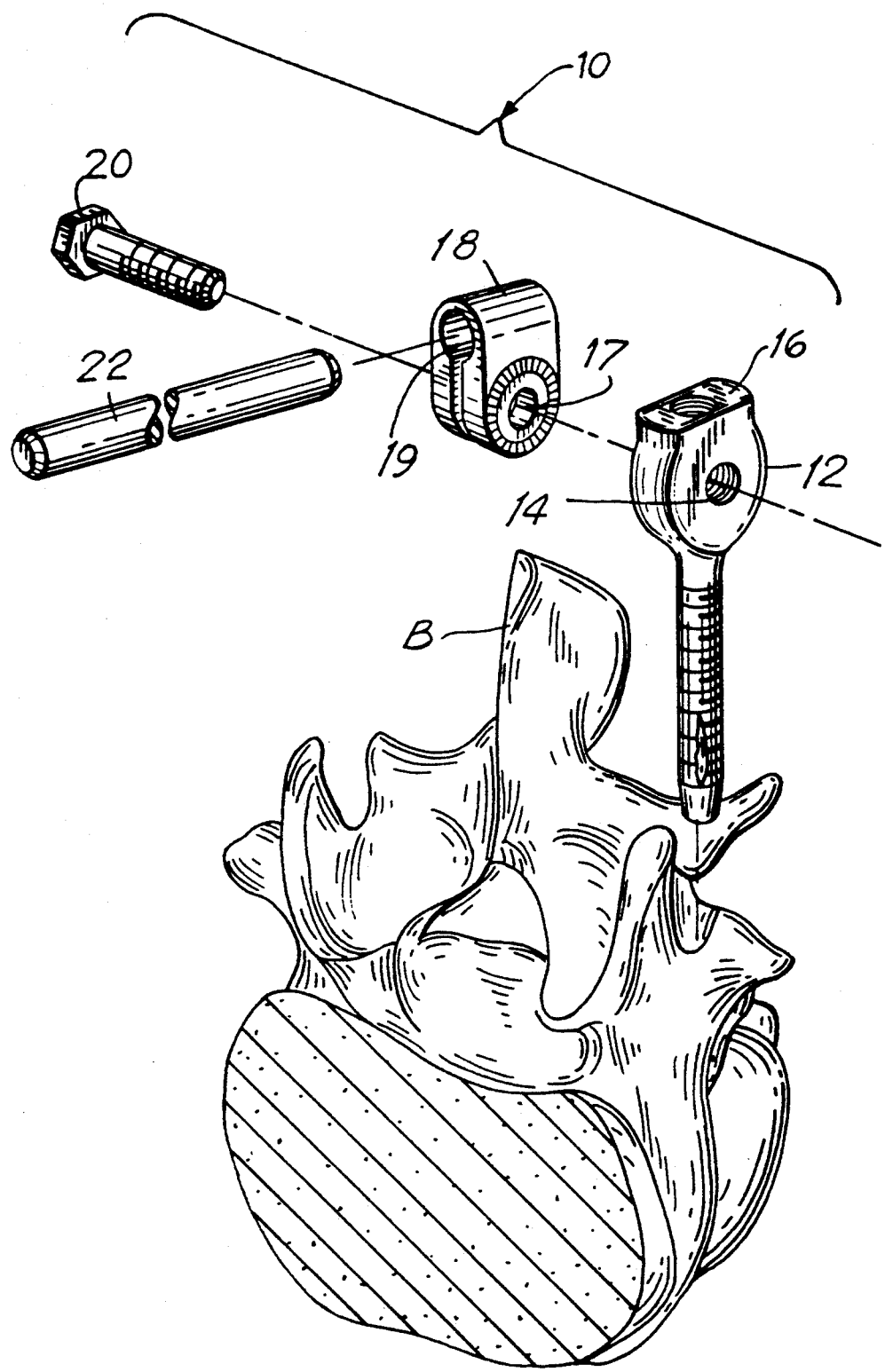
FIG. 8 is an exploded view illustrating the components of the Vermont Spinal Fixator implant and their relationship to a vertebra.

Bevel gear 96 is formed integrally with socket 104 and rides on shaft pin 102. In a preferred embodiment, socket 104 is designed to receive a hex-head threaded fastener. Arms 32 and 34 function as shown and described in FIGS. 1 and 2. Engaging members 36 and 38 have flattened sides in FIGS. 6 and 7; however, they cooperate with articulating clamp bore 19 as previously described.

The use of both wrench 100 and 200 is generally the same. The surgeon places clamp bolt 20 through hole 17 in articulating clamp 18. Articulating clamp 18 is then forced between engaging members 36 and 38 which are biased together by arms 32 and 34. The biasing force of arms 32 and 34 is sufficient to firmly hold articulating clamp 18 in place, however not so great that the wrench may not be easily removed once clamp bolt 20 is secured in the pedicle screw 12.

With the articulating clamp and clamp bolt installed on the wrench as shown in FIG. 4, the surgeon may simply align clamp bolt 20 with threaded hole 14 in pedicle screw 12 and drive the bolt into threaded hole 14 by rotation of wheel 28 or 100. This arrangement insures that clamp bolt 20 is held firmly in socket 40 or 104 as it is driven into the pedicle screw. There is no necessity for the surgeon to place his fingers actually in the incision around the pedicle screw in order to guarantee proper starting of clamp bolt 20.

Depending on a number of factors, including the patient's size and the particular vertebra involved, initially there may not be sufficient room to fit even the wrench according to the present invention between the pedicle screw and spinous process, with the articulating clamp and clamp bolt attached. This interference may be avoided by rotating the pedicle screw a small amount, approximately one quarter (¼) of one rotation or less, in a direction which positions the face of the pedicle screw receiving the clamp bolt slightly caudally. 45° will generally be an appropriate rotation, although, depending on the particular case, rotation may be between about 20°-80°. This will provide adequate clearance for the initial installation of the clamp bolt. Once the clamp bolt has been screwed in a short distance, the pedicle screw may be finally positioned without interference between the wrench and the spinous process. Clamp bolt 20 then may be tightened as required and the wrench subsequently removed.

The detailed description of the preferred embodiments contained herein is intended to in no way limit the scope of the invention. As will be apparent to a person of ordinary skill in the art, various modifications and adaptions of the structure above described will become readily apparent without departure from the spirit and scope of the invention, the scope of which is defined in the appended claims.

What is claimed is:

1. Apparatus for installing a first part on a second part utilizing a threaded fastener passing through said first part and engaging said second part, said apparatus comprising:
    a body;
    drive means for applying torque to said threaded fastener, said drive means rotatably mounted in said body and including socket means for receiving the threaded fastener; and
    means for holding said first part adjacent to said body with said threaded fastener passing through the first part and received in said socket means, said holding means configured and dimensioned to position said first part sufficiently close to said socket means to retain the threaded fastener therein and wherein said drive means is rotatable with respect to said holding means, whereby said first part may be installed on said second part without the necessity of a person touching or separately holding said first part after it is held by said holding means.

2. Apparatus according to claim 1, wherein said holding means includes two adjacent arms, extending from one side of the body in the direction of said drive means, said arms being adapted to biasly engage the first part between them.

3. Apparatus according to claim 2, wherein said arms terminate in spherical members for cooperating with and engaging an associated bore in the first part.

4. Apparatus according to claim 1, further comprising:
    a drive gear mounted in said body and capable of being rotated by an externally applied force;
    a driven gear mounted in said body, driven by said drive gear and including said drive means, wherein said drive means comprises a socket formed in said driven gear, said socket being adapted to directly engage said threaded fastener without an adapter or other intermediate tool; and
    at least one intermediate gear transmitting torque from the drive gear to the driven gear, wherein at least one of said gears is mounted to be axially slidable on a shaft to provide clearance for cleaning between said at least one gear and said body.

5. Apparatus according to claim 4, wherein said socket is a hex-socket for receiving a hex-head threaded fastener.

6. Apparatus according to claim 4, further comprising means for manual rotation of said drive gear whereby said threaded fastener may be torqued by manually rotating said means.

7. Apparatus according to claim 4, wherein the drive gear, said at least one intermediate gear and the driven gear are spur gears and torque is transmitted from said drive gear to said driven gear by a meshing gear train mounted in said body including said least one intermediate gear.

8. Apparatus according to claim 7, wherein said meshing gear train includes:
    four first spur gears, one of said first gears engaging the drive gear and each first gear engaging another first gear; and
    three second spur gears one of said second gears engaging said driven gear and another of said second gears engaging one of said first gears and each second gear engaging another second gear;
    wherein said first gears have a pitch radius greater than approximately two times the pitch radius of said second gears.

9. Apparatus according to claim 7, having an overall thickness of less than ⅜ inch at said drive means in a direction parallel with the axis of said driven gear.

10. Apparatus for installing a first part on a second part utilizing a threaded fastener passing through said first part and engaging said second part, said apparatus comprising:
    a body;
    a driven gear mounted in said body, said driven gear having drive means for directly engaging said threaded fastener without an adapter or other intermediate tool;
    a drive gear for transferring externally applied torque to said driven gear; and
    means for holding said first part adjacent to said body with said threaded fastener passing therethrough and engaging said drive means, said holding means including two adjacent arms disposed on and extending from one side of the body in the direction of said driven gear, wherein said one side defines a plane substantially parallel therewith and said arms are adapted to exert a biasing force on said first part along a line substantially parallel to said plane to biasly engage said first part between said two arms and wherein said driven gear is rotatable with respect to said holding means.

11. Apparatus according to claim 10, wherein the drive gear and driven gears are bevel gears which directly engage each other, and said drive gear is mounted on a shaft extending through said body and protruding from said body at an end opposite said driven gear, whereby said shaft may be rotated to transmit torque to said drive means.

12. Apparatus according to claim 10, wherein said drive means includes a socket formed in said driven gear and configured to receive a head of the threaded fastener.

13. Apparatus according to claim 10, wherein said drive gear and said driven gear are spur gears and said apparatus further comprises a plurality of spur gears located between said driven gear and said drive gear, forming a meshing gear train for transmitting torque from said drive gear to said driven gear.

14. Apparatus according to claim 10, wherein said driven gear is rotatably mounted on and retained by a shaft extending from only one side of said driven gear, said shaft having an enlarged diameter portion at a first end, said enlarged diameter portion received in a central recess in said driven gear and said shaft having a second end received in a bore in said body.

15. Apparatus according to claim 10, wherein said drive gear and said driven gears are bevel gears which engage directly with each other.

16. Apparatus according to claim 10, wherein said drive gear is rotatable by means of a wheel mounted external to said body.

17. Apparatus according to claim 10, wherein said arms are provided with spherical members for cooperating with and engaging an associated bore in said first part.

18. A surgical tool for installing a first part of a spinal fixation implant on a second part of the implant with a threaded fastener, said second part having a threaded hole for receiving said fastener and said second part being implanted in a pedicle of a vertebrae spaced laterally a short distance from the spinous process, and wherein said first part defines a first bore for receiving said fastener and a second bore offset from said first bore and disposed perpendicular to said first bore, said tool comprising:
 a body;
 a driven gear mounted for rotation in said body, said driven gear having a socket formed therein for directly receiving said fastener without an adapter or other intermediate tool, said driven gear and socket having a minimum profile to allow said tool, with said bolt in said socket, to be positioned between the second part and the spinous process;
 a drive gear for transferring torque to said driven gear;
 means for applying torque to the drive gear; and
 two adjacent arms extending from one side of the body in the direction of the socket, said arms provided with means for biasly engaging said second bore in said first part between said arms to hold said first bore in alignment with said socket, whereby said threaded fastener may be placed through the first bore in the first part and the first part may be engaged and held by said tool with said fastener received in said socket to allow a surgeon to install the first part on the second part with the threaded fastener and without handling either the first or second part after the first part is held by said tool.

19. Method for installing a spinal fixation implant on a vertebra of a spinal column comprising:
 implanting a screw in a pedicle of the vertebra spaced laterally a short distance from the spinous process, said screw having a threaded hole perpendicular to the screw axis and adjacent the screw head;
 placing a threaded fastener and a part to be joined to the pedicle screw with said fastener in engagement with a tool, wherein said tool has a rotatable socket and said threaded fastener is received in said socket for transferring torque to said fastener, and said part is held by said tool with said fastener passing through a bore in said part, said tool having means remote from said socket for rotating said socket and applying torque to said fastener;

manipulating the tool approximately between the spinous process and the pedicle screw to engage the fastener with the threaded hole in the pedicle screw;
 applying torque to the threaded fastener to screw said fastener into the threaded hole in the pedicle screw; and
 removing the tool and leaving behind the part and the fastener fixed to the pedicle screw.

20. The method according to claim 19, wherein said threaded hole defines a central axis perpendicular to the screw axis with half of said central axis extending towards the spinous process, said method further comprising:
 rotating the pedicle screw to position said central axis half between about 20°–80° caudally with respect to a line perpendicular to the spinal column, said rotation being prior to engaging said threaded fastener with said threaded hole; and
 rotating the pedicle screw to position said half of the central axis approximately parallel to said perpendicular line after the threaded fastener has been driven at least partially into said threaded hole.

21. The apparatus according to claim 4, wherein:
 the body comprises an upper member and a lower member defining a space therebetween having a height, with said gears disposed in said space; and
 at least one gear has a thickness greater than one half the height of the space but substantially less than the full height of the space, whereby said cleaning clearance can be slightly less than the gear thickness while ensuring that said gear contacts is neighboring gears.

22. Apparatus for installing a fist part on a second part utilizing a threaded fastener passing through said first part and engaging said second part, said apparatus comprising:
 a body;
 drive means for receiving and applying torque to said threaded fastener, said drive means rotatably mounted in said body; and
 means for holding said first part adjacent to said body with said threaded fastener passing through the first part and received in said drive means, wherein said holding means includes two adjacent arms extending from one side of the body in the direction of said drive means and terminating in spherical members for cooperating with and engaging an associated bore in the first part, said arms being adapted to biasly engage the first part between them, whereby said first part may be installed on said second part without the necessity of a person touching or separately holding said first part after it is held by said holding means.

23. Apparatus for installing a first part on a second part utilizing a threaded fastener passing through said first part and engaging said second part, said apparatus comprising:
 a body;
 a drive gear mounted in said body and capable of being rotated by an externally applied force;
 a driven gear rotatably mounted in said body, driven by said drive gear and including drive means for receiving and applying torque to said threaded fastener;
 a meshing gear train mounted in said body for transmitting torque from the drive gear to the driven gear, said meshing gear train including a plurality of first spur gears, one of said first gears engaging the drive gear and each first gear engaging another first gear, and a plurality of second spur gears, one of said second gears engaging said driven gear and another of said second gears engaging one of said first gears and each second gear engaging another second gear, wherein said first gears have a pitch radius greater than approximately two times the pitch radius of said second gears; and means for holding said first part adjacent to said body with said threaded fastener passing through the first part and received in said drive means, whereby said first part may be installed on said second part without the necessity of a person touching or separately holding said first part after it is held by said holding means.

* * * * *